(12) United States Patent
Liu et al.

(10) Patent No.: US 8,738,116 B2
(45) Date of Patent: May 27, 2014

(54) METHOD AND APPARATUS FOR PERIODONTAL DIAGNOSIS

(75) Inventors: Kan-Zhi Liu, Winnipeg (CA); Mike G. Sowa, Winnipeg (CA)

(73) Assignee: National Research Council of Canada, Ottawa (CA)

( * ) Notice: Subject to any disclaimer, the term of this patent is extended or adjusted under 35 U.S.C. 154(b) by 902 days.

(21) Appl. No.: 12/733,663

(22) PCT Filed: Sep. 22, 2008

(86) PCT No.: PCT/CA2008/001645
§ 371 (c)(1),
(2), (4) Date: Jun. 14, 2010

(87) PCT Pub. No.: WO2009/036561
PCT Pub. Date: Mar. 26, 2009

(65) Prior Publication Data
US 2010/0280392 A1   Nov. 4, 2010

Related U.S. Application Data

(60) Provisional application No. 60/960,249, filed on Sep. 21, 2007.

(51) Int. Cl.
*A61B 6/14* (2006.01)

(52) U.S. Cl.
USPC ......................................... 600/475; 600/473

(58) Field of Classification Search
USPC ................................. 600/473–476
See application file for complete search history.

(56) References Cited

U.S. PATENT DOCUMENTS

| 5,570,182 | A | 10/1996 | Nathel et al. |
| 6,594,513 | B1 | 7/2003 | Jobsis et al. |
| 2001/0016760 | A1 | 8/2001 | Irion et al. |
| 2001/0041964 | A1* | 11/2001 | Grass et al. ............ 702/19 |
| 2002/0072676 | A1* | 6/2002 | Afanassieva ............ 600/473 |
| 2005/0234526 | A1 | 10/2005 | Gilhuly et al. |
| 2008/0076983 | A1* | 3/2008 | Debreczeny et al. ...... 600/310 |
| 2008/0260650 | A1* | 10/2008 | Tawakol et al. .......... 424/9.37 |

FOREIGN PATENT DOCUMENTS

| EP | 0 049 905 A1 | 10/1981 |
| EP | 0049905 | 10/1981 |
| EP | 1 677 095 A1 | 5/2006 |
| EP | 1677095 | 5/2006 |
| WO | 0106915 | 2/2001 |
| WO | WO 01/06915 A1 | 2/2001 |

OTHER PUBLICATIONS

Huynh et al., "Specific fibronectin fragments as markers of periodontal disease status", J. Periodontol, 2002, vol. 73(10), p. 1101-1110.

(Continued)

*Primary Examiner* — Tse Chen
*Assistant Examiner* — Rochelle Reardon
(74) *Attorney, Agent, or Firm* — Catherine Lemay (57) ABSTRACT

A technique for obtaining information regarding a state of periodontal tissue involves deriving a substantially whole curve measure of similarity of an observed bandshape of an isolated spectral component attributed to water within the infrared region. Subtle variations in the bandshape of the water bands have been found to correlate with inflammatory periodontal diseases and using whole curve measures such as weighted integrals or measure of fit parameters these variations can be detected and used to classify periodontal tissues.

23 Claims, 5 Drawing Sheets

(56) References Cited

OTHER PUBLICATIONS

Sowa et al., "Semi-Parametric Estimation in the Compositional Modeling of Multicomponent Systems from Raman Spectroscopic Data", Appl. Spectrosc., 2006, vol. 60(8), p. 877-883.
Sowa et al., "Classification of burn injuries using near-infrared spectroscopy", J. Bio. Optics., 2006, vol. 11(5), p. 054002-1-054002-6.
Araki et al., "The effect of hyperbaric oxygen on cerebral hemoglobin oxygenation and dissocation rate . . . ", Adv. Exp. Med. Bio., 1988, vol. 222, p. 375-381.
Eley et al., "Advances in periodontal diagnosis. 8. Commerical diagnostic kits based on GCF proteolytic and hydrolytic enzyme levels", Br Dent J., 1998; vol. 184(8), p. 373-6.
Loee et al., "Periodontal Disease in Pregnancy. I. Prevalence and Severity", Acta Odontol Scand.,1963, vol. 21, p. 533-551.
Martin K., "In vivo measurements of water in skin by near-infrared reflectance", Applied Spectroscopy, 1998, vol. 52, p. 1001-1007.
Otal et al., "Monitoring the temperature of dilute aqueous solutions using near-infrared water absorption" Appl Spectrosc., 2003, vol. 57, p. 661-666.
Takaishi et al., "The benzoyl-DL arginine-naphthylamide (BANA) test and polymerase chain reaction measurement . . . ", Int J Tissue React., 2003, vol. 25, p. 19-24.
Armitage et al., "Periodontal Diseases: Diagnosis", Ann. Periodontol, 1996, vol. 1, p. 37-215.
Armitage et al., "Diagnosis of Periodontal Diseases", J. Periodontol, 2003, vol. 74, p. 1237-1247.
Attas et al., "Visualization of cutaneous hemoglobin oxygenation and skin hydration using near infrared spectroscopic imaging", Skin Res. Tech., 2001, vol. 7, p. 238-245.
Attas et al., "Near-IR spectroscopic imaging for skin hydration: the long and the short of it", Biopolymers (Biospectroscopy), 2002, vol. 67, p. 96-106.
Borden et al., "Tobacco-induced alterations to the Fourier-transform infrared spectrum of serum", J Mol Med., 2003, vol. 81, p. 788-794.
Brown et al., "Prevalence, extent, severity and progression of periodontal disease", Periodontol 2000, 1993, vol. 2, p. 57-71.
Brown et al., "Receiver operating characteristics curves and related decision measures", Chemometrics Intellig Lab Systems, 2006, vol. 80, p. 24-38.
Burt B., "Position Paper: Epidemiology of Periodontal Diseases", J. Periodontol, 2005, vol. 76, p. 1406-1419.
Chun et al., "Biological foundation for periodontitis as a potential risk factor for atherosclerosis", J Periodontal Res., 2005, vol. 40, p. 87-95.
Greenstein G., "Commentary on periodontal diagnostic testing", J. Periodontol, 1995, vol. 66, p. 531-535.
Hanioka et al., "Hemoglobin concentration and oxygen saturation of clinically healthy and inflamed gingiva in human subjects", J Periodontal Res., 1990, vol. 25, p. 93-98.
Huynh et al., "Specific fibronectin fragments as markers of periodontal disease status", J. Periodontol, 2002, vol. 73 (10), p. 1101-1110.
Lamster et al., "Analysis of gingival crevicular fluid as applied to the diagnosis of oral and systemic diseases", Ann N Y Acad Sci, 2007, vol. 1098, p. 216-229.
Liu et al., "Near Infrared Spectroscopy Determines Multiple Indices of Inflammation In Vivo", ppt presentation, 2006.
Liu et al., "Near Infrared Spectroscopy Determines Multiple Indices of Inflammation In Vivo", For J. of Clinical Periodontol., Submission date Sep. 20, 2005.
Loesche et al., "The optimization of the BANA test as a screening instrument for gingivitis among subjects . . . ", J. Clin. Periodontol, 1997, vol. 24, p. 718-26.
Maiden et al,. "Subgingival temperature and microbiota in initial periodontitis", J Clin Periodontol.,1998, vol. 25, p. 786-793.
Morita et al., "Relationship of sulcular sulfide level to severity of periodontal disease and BANA test", J. Periodontol, 2001, vol. 72, p. 74-8.
Moutsopoulos et al., "Low-grade inflammation in chronic infectious diseases: paradigm of periodontal infections" Ann N Y Acad Sci., 2006, vol. 1088, p. 251-264.
Nozaki et al., "A sensitive method for detecting porphyromonas gingivalis by polymerase chain reaction.", J Periodontol, 2001, vol. 72, p. 1228-1235.
Palmer et al., "Mechanisms of action of environmental factors—tobacco smoking", J Clin Periodontol., 2005, vol. 32, Suppl 6, p. 180-195.
Pavolotskaya et al., "Sulcular sulfide monitoring: an indicator of early dental plaque-induced gingival disease", J. Dent. Hyg., 2006, vol. 80, p. 11.
Prescher et al., "Rapid quantitative chairside test for active MMP-8 in gingival crevicular fluid: first clinical data", Ann N Y Acad Sci., 2007, vol. 1098, p. 493-495.
Ridder et al., "Noninvasive alcohol testing using diffuse reflectance near-infrared spectroscopy", Applied Spectroscopy, 2005, vol. 59(2), p. 181-189.
Rosin et al., "Quantification of gingival edema using a new 3-D laser scanning method", J Clin Periodontol., 2002, vol. 29, p. 240-246.
Schacher et al., "Aggregatibacter actinomycetemcomitans as indicator for aggressive periodontitis by two analysing strategies" J Clin Periodontol., 2007, vol. 34, p. 566-573.
Scott et al., "Suppression of overt gingival inflammation in tobacco smokers—clinical and mechanistic considerations", Int J Dent Hyg., 2004, vol. 2, p. 104-110.
Socransky et al., "New concepts of destructive periodontal disease", J Clin Periodontol., 1984, vol. 11, p. 21-32.
Sorsa et al., "Scientific basis of a matrix metalloproteinase-8 specific chair-side test for monitoring periodontal . . . ", Ann N Y Acad Sci., 1999, vol. 878, p. 130-40.
Sowa et al., "Near infrared spectroscopic assessment of tissue hydration following surgery", J of Surg Res.,1999, vol. 86, p. 62-69.
Sowa et al., "Near infrared spectroscopic assessment of hemodynamic changes in the early post-burn period", Burns 2001, vol. 27, p. 241-249.
Sowa et al., "Spectroscopic assessment of cutaneous hemodynamics in the presence of high epidermal melanin concentration", Clin Chim Acta., 2002, vol. 317, p. 203-212.
Sowa et al., "Semi-Parametric Estimation in the Compositional Modeling of Multicomponent Systems from Raman Spectroscopic Data", Appl. Spectrosc., 2006a, vol. 60(8), p. 877-883.
Sowa et al., "Classification of burn injuries using near-infrared spectroscopy", J. Bio. Optics., 2006b, vol. 11(5), p. 054002-1-054002-6.
Teng et al., "Periodontal health and systemic disorders", J Can Dent Assoc., 2002, vol. 68, p. 188-192.
International Preliminary Report on Patentability dated Dec. 23, 2008 for PCT/CA2008/001645.
International Search Report and Written Opinion dated Nov. 27, 2008 for PCT/CA2008/001645.
Bowers et al., "Connective tissue-associated proteins in crevicular fluid: potential markers for periodontal diseases", J. Periodontol, 1989, vol. 60, p. 448-451.
Lamster et al., "Evaluation of components of gingival crevicular fluid as diagnostic tests", Ann. Periodontol, 1997, vol. 2, p. 123-37.
Taba et al., "Diagnostic biomarkers for oral and periodontal diseases", Dent Clin North Am., 2005, vol. 49, p. 551-571.
Snyder et al., "Analytical performance of an immunologic-based periodontal bacterial test for simultaneous detection . . . ", J Periodontol., 1996, vol. 67, p. 497-505.

\* cited by examiner

METHOD AND APPARATUS FOR PERIODONTAL DIAGNOSIS

This application is a national entry of PCT/CA2008/001645 filed Sep. 22, 2008, which claims the benefit of U.S. Provisional Patent Application U.S. Ser. No. 60/960,249 filed Sep. 21, 2007, which is herein incorporated by reference in its entirety.

FIELD OF THE INVENTION

BACKGROUND OF THE INVENTION

Gingivitis is a reversible infectious disease of the periodontia characterized by an inflamed periodontia that bleeds readily. Periodontitis is an infectious, destructive inflammatory disease of the soft and hard tissues surrounding the teeth and is the leading cause of edentulism. Moderate periodontitis occurs in a majority of adults, while the prevalence of severe, generalized disease is in the region of 10%.[1] Increasing evidence suggests that periodontitis may be associated with increased risk of vascular diseases (including coronary artery disease and stroke), diabetes mellitus, lung diseases (COPD and pneumonia), and pre-term delivery.[2-4]

Periodontitis is currently diagnosed on gross clinical manifestations, i.e. signs of gingival inflammation (e.g. redness, swelling), periodontal pocketing, and periodontal attachment or alveolar bone loss.[5] Such manifestations are measured by periodontal probing and radiographs. Alveolar bone and periodontal attachment loss represent the results of the destructive aspects of host defense mechanisms responding to the microbial plaque biofilm present in the gingival sulcus, as well as the direct effects of virulence factors of periodontal pathogens. Longitudinal studies have indicated that progression of chronic periodontitis, in terms of loss of periodontal attachment, is infrequent and episodic, and most progression occurs in a smaller proportion of highly susceptible individuals.[1,6] Furthermore, traditionally used diagnostic procedures (clinical signs) do not distinguish between disease-active and disease-inactive sites. In other words, without long-term longitudinal assessment, it cannot be determined if periodontal destruction is current or a reflection of past disease.[5,7] Unfortunately tools for such longitudinal studies are not available. Thus, major diagnostic and prognostic problems exist for periodontitis.

Potential diagnostic tests that have been studied include: (a) the presence of specific bacteria (including *Porphyromonas gingivalis* and *Aggregatibacter actinomycetemcomitans*),[8,9] or (b) their products (e.g. volatile sulfur compounds and proteolytic enzymes),[10,11] (c) biomarkers which are involved in the disease process but produced by the host (e.g. matrix metalloproteinase-8,[12] neutrophil elastase; aspartate aminotransferase; glucuronidase; and alkaline phosphatase,[13] (d) biomarkers that occur as a consequence of tissue damage (e.g. collagen fragments),[14] and (e) other markers of the inflammatory process e.g. subgingival temperature probes; prostaglandin E2; and interleukin-1.[13-15]

To date, however, the predictive value of all potential markers has not been high enough for routine use in clinical practice. In addition, most diagnostic methods that have been investigated are too complicated for routine chair-side use. Furthermore, due to the complex nature of periodontitis—which involves a multifaceted immune and inflammatory reaction to a polymicrobial flora—a composite analytical approach to tissue and/or gingival crevicular fluid analysis is much more likely to prove successful than analysis of one or, at best, a few individual biomolecules.

If diagnosis using spectroscopy is viable, it would be widely applicable in dentistry. In general, spectroscopy is an attractive technology to apply to the study of periodontal inflammation and periodontal diseases as spectra can be captured instantly, no consumables need be purchased or developed (such as antibodies, substrates, or molecular probes), and, once the equipment is in place, it is very inexpensive to operate. Furthermore, commercially available portable spectrometers are small, they do not require cryogenic cooling, and therefore, can be readily utilized in small clinical environments, such as a periodontal operatory, and require minimal training to obtain reliable and reproducible data. Additionally, it is an entirely non-invasive technique that uses low energy radiation. Future studies are warranted that will establish the spectra that are characteristic of healthy and diseased periodontal sites in individual subjects with gingivitis and/or periodontitis.

Furthermore, the successful application of NIR spectroscopy to the study of periodontitis could provide great potential research benefits. It is generally accepted that the accuracy, reproducibility, and validity of the clinical index reporting are sensitive to subjective components.[32] Indeed, Rosin et al.[32] point out that non-invasive inflammatory indices (redness and edema) are even more susceptible to the negative influence of subjectivity than invasive measures. Thus, we propose that spectroscopy could conceivably represent a means of standardization of clinical measures of inflammation in periodontal tissues. Such standardized methods would have obvious benefits to both clinical studies and mechanistic studies.

EP 0 049 905 to Schief teaches a device for measuring gingival color intended especially for assessing gingival diseases. It provides that the light of a light source is fed via an optical fiber to a probe and illuminates the gingival tissue at the outlet. Via a second returning optical fiber, the reflected light is evaluated in a plurality of wavelength regions by means of filters, and fed to photoelectric components. The signals are then evaluated in an electronic device. It is not explicitly stated in the Schief patent which wavelength bands are examined, but it appears that the filters are chosen to detect blood flow with the measurement of deoxyhemoglobin and oxyhemoglobin.

U.S. Pat. No. 5,570,182 to Nathel et al. teaches the assessment of gingivitis by non-ionizing radiation. Specifically, Nathel et al. teach the mapping of a periodontal pocket to determine an attachment level of a tooth as well as alveolar bone level. Nathel et al. also teach absorption spectral analysis of teeth to distinguish active or inactive cavities from healthy teeth.

Several absorption bands in the visible and near infrared (NIR) spectral region reflect key inflammatory events.[16,17] For instance, tissue edema—an index that is commonly used as a marker of gingival inflammation[16,19]—can be measured using MR spectroscopy.[16,17] Thus, monitoring the intensity of the water bands in gingival tissues is expected to provide an index of tissue hydration representing a simple indicator of inflammation at specific periodontal sites.

In addition to measuring tissue water intensity, spectroscopy offers a non-invasive means of assessing the balance between tissue oxygen delivery and oxygen utilization. Hemoglobin and oxygenation indices have been previously measured in periodontal tissues with the data suggesting that the increase in blood supply during inflammation is insufficient to meet the oxygen demand in inflamed gingivae.[21] The electronic transitions stemming from the heme ring and central metal ion of hemoglobin are particularly strong in the visible region. Spectroscopy can measure relative concentrations of oxygenated hemoglobin ($HbO_2$) and deoxygenated (Hb) hemoglobin by fitting optical attenuation spectra to the known optical properties (extinction coefficients) of $HbO_2$ and Hb.[17,22] Thus, spectroscopy provides a measure of the hemoglobin oxygen saturation of tissues and the degree of tissue perfusion.

Increased hemoglobin levels are indicative of an increased blood perfusion, which, if severe enough, is clinically reflected in bleeding on probing. We have been able to use NIRS to show increased tissue perfusion in diseased tissues by monitoring hemoglobin dynamics. Thus, due to the strong signatures of hemoglobin molecules in the MR spectrum, NIRS provides a reliable indicator of both clinically-evident and sub-clinical tissue perfusion. We have also been able to use NIRS to show that oxygen saturation is significantly decreased in diseased periodontal tissues.

Tissue hypoxia occurs because of increased oxygen consumption by host cells during inflammatory reactions. Interestingly, it has been shown previously that tissue oxygen saturation correlates well with oxygen tension in periodontal pockets[21] and the progression of inflammatory disease is known to be dependent upon infection with a complex microflora whose climax community is dominated by Gram negative anaerobic bacteria. Tissue oxygen saturation is not currently measured clinically, NIRS can provide a further index of inflammation that may prove useful to the periodontist. This suggests that spectroscopy has the potential to diagnose and assess inflammatory periodontal diseases.

Furthermore, the 960 nm water band is known to shift with tissue temperature and changes in electrolyte concentration.[20]

Given the inadequacies of current techniques, there is a need for the development of a non-invasive technique for diagnosing periodontitis and other inflammatory diseases of the peridontia. Particularly desirable are diagnostic and prognostic tests having the following features:

1—simplicity and user friendliness which leads to easy training and reliable test results (low variability of results in dependence upon the tester),
2—low consumable, reagent-free application for minimizing costs associated with storage, spoilage, etc.,
3—chair-side applicability with equipment that is not massive, inordinately expensive, complex, susceptible to damage or malfunction, excessively sensitive to operating conditions, etc., and
4—targeted for site-specific diagnosis as opposed to a systemic test.

SUMMARY OF THE INVENTION

It is not generally known whether an effective test for periodontal diseases can be produced using only spectral absorption information within the near infrared spectrum (herein a region between 700-2500 nm wavelengths). It is not generally known how well the multiple indicators of diseased states manifest in periodontal tissues can be detected from single spectral traces, and further it is not known what spectral features correlate with various disease states.

Applicant has found excellent correlation of spectral features with diseased states, a surprising fact given the length of time spectral analysis has been known and identifiers of periodontal diseases has been sought. More specifically Applicant has found that the moments of the water bands correlate with inflammatory periodontal diseases, including periodontitis, and therefore demonstrably provide a marker for the presence of disease.

Accordingly, a method is provided for obtaining data regarding a state of periodontal tissue. The method involves obtaining from the tissue, spectral absorption data of at least part of the infrared spectrum, identifying from the data a bandshape of a spectral component attributed to water, and deriving a substantially whole curve measure of the bandshape that varies with a state of the water molecules in the band. The measure provides an indicator of a condition of the tissue, and is preferably at least a contributory indicator of one of periodontitis, peri-implantitis and peri-implant mucositis. Applicant has verified that bandshape properties vary with periodontitis.

The spectral component may be one of a OH stretching overtone/combination band, and a OH stretch-bend combination band, and as such may have a spectral range including at least a significant part of one or more of the following spectral ranges: 900-1100 nm, 1380-1560 nm, and 1800-2000 nm. Applicant has investigated the water band within the 900-1100 nm, and 1380-1560 nm, ranges, and has demonstrated correlation of the 900-1100 nm with clinically determined periodontitis.

Obtaining the spectral absorption data may involve illuminating the tissue with light of at least two wavelengths within a spectral range of the spectral component, and determining absorption values of each of the at least two wavelengths. In this case, identifying from the data a bandshape of a spectral component attributed to water, may involve fitting the absorption values to one of a plurality of known curves for the spectral components to extrapolate the bandshape from the absorption values, and deriving the substantially whole curve measure may involve identifying the indicator of the condition of the tissue according to a measure of fit of the absorption values to the known curves.

Preferably obtaining the spectral absorption data comprises illuminating the tissue with a broadband emitter that emits light within at least a substantial part of the spectral range of the spectral component, and the absorption of the spectral component is sampled throughout the part of the spectral range to obtain a spectral trace. If so, identifying the spectral component attributed to water may involve decomposing the spectral trace to remove from the spectral trace contributions from respective other components known to absorb at wavelengths in the part of the spectral range, in order to obtain the bandshape attributed to water. For example, decomposing the spectral trace may involve applying a Beer-Lambert unmixing model, in which quantified amounts of the other known constituents are removed from the signal.

Deriving a substantially whole curve measure of the bandshape may involve comparing the bandshape to at least one known curve for the spectral component, and identifying the indicator of the condition of the tissue according to a measure of similarity of the bandshape to the known curve. Alternatively, deriving a substantially whole curve measure of the bandshape may involve integrating the bandshape with a weighting function that weights wavelengths distant from a peak significantly differently than wavelengths near the expected peak. The integral may be a moment of the bandshape about a given wavelength, such as a moment about one of an expected peak wavelength of the spectral component, a mean peak wavelength of the spectral component of tissue of a given condition, and a computed peak of the spectral trace. Applicant has found the first moment about an expected peak wavelength of the spectral component to be correlated with periodontitis.

Also an article is provided, the article having a computer readable modulated carrier signal and program instructions encoded on said signal for: receiving a bandshape of a spectral component attributed to water identified from infrared absorption spectral data of a periodontal tissue; and deriving a substantially whole curve measure of the bandshape that varies with a state of the water molecules in the band, to provide an indicator of a condition of the tissue as healthy or subject to an inflammatory disease.

The program instructions derive the substantially whole curve measure by: comparing the bandshape with at least one known curve for the spectral component, and identifying the indicator of the condition of the tissue according to a measure of similarity of the bandshape to the known curve; or integrating the bandshape with a weighting function that weights wavelengths distant from an expected peak significantly differently than wavelengths near the expected peak. The program instructions may be further adapted to preprocess spectral absorption data, or decompose a spectral trace to remove from the spectral trace contributions from respective other components known to absorb at wavelengths to obtain the bandshape attributed to water.

Furthermore, an apparatus is provided for obtaining data regarding a state of periodontal tissue. The apparatus includes a processor having program instructions for: receiving spectral absorption data of at least part of the infrared spectrum from the tissue; identifying from the data a bandshape of a spectral component attributed to water; and deriving a substantially whole curve measure of the bandshape that varies with a state of the water molecules in the band, to provide an indicator of a condition of the tissue as healthy or subject to an inflammatory disease. The spectral component may be one of a OH stretching overtone/combination band, and a OH stretch-bend combination band, and may have a spectral range including at least a significant part of one or more of the following spectral ranges: 900-1100 nm, and 1380-1560 nm.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

A method and apparatus for identifying inflammatory diseased states of periodontal tissues is provided, including periodontitis, peri-implantitis and peri-implant mucositis.

The experiment described below clearly demonstrates that water band absorption peak wavelength and bandwidth variations are correlated with periodontitis. This is not at all an expected result, especially given that the amplitude of the water band absorption peaks was substantially non-correlated with disease states of the tissues, and given the number of factors attendant to the disease and the number of factors that may be postulated to cause shifts and broadening/narrowing of these bands.

Applicant has further shown that a spectroscopic system can be used to acquire spectra from periodontal tissues and that the data extracted from these spectra provide detailed site-specific information on multiple aspects of periodontal inflammation concurrently. Thus in a preferred embodiment, Applicant would use a plurality of markers of diseased state to determine a condition of the tissue at a site, including tissue oxygenation measures. Site-specific variations in a number of inflammatory indices were concurrently measured, including total oxygen saturation; deoxygenated hemoglobin, and water band absorption moments.

Apparatus

Figure 1:
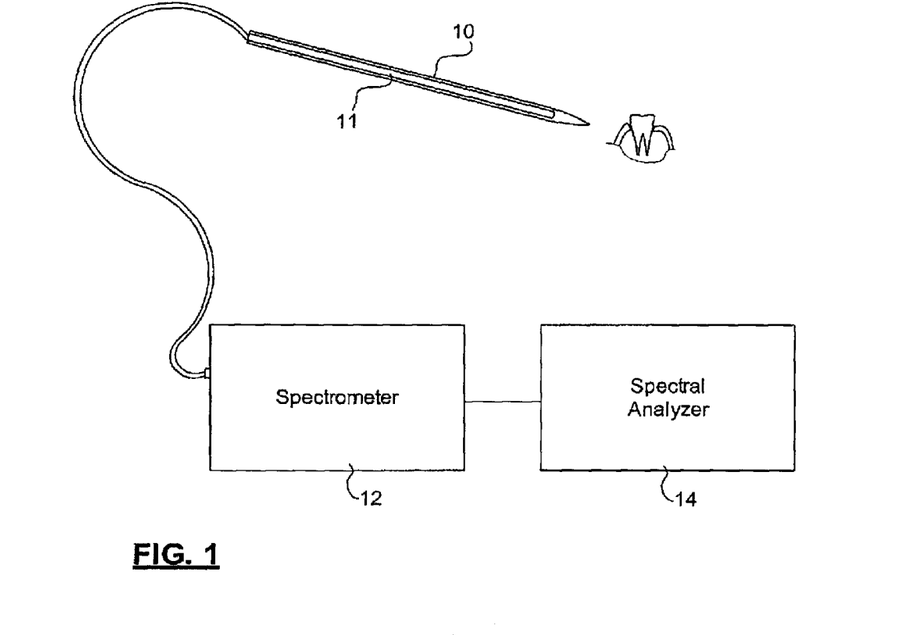
FIG. 1 is a schematic illustration of an apparatus for spectral analysis of periodontal tissue.

Applicant does not believe that the useful results demonstrated by the apparatus below is correctly attributed to the particular spectroscopic system used, and that, subject of course to the natural limits of quality and resolution, any other spectroscopic system operable within the near infrared (NIR) spectrum could be used. Accordingly, Applicant provides an apparatus for determining a disease state of a periodontal site, as shown in FIG. 1. The apparatus consists of a probe 10 having at least one waveguide 11. Light reflected from the site is collected and transmitted through the waveguide 11 to a spectroscope 12. As is well known in the art, the probe 10 may include a bundle of fiber optic cables and one or more of these may be used for illuminating the site with light from a source having at least a plurality of wavelengths, and may provide multiple waveguides for providing multiple paths for independently collected and transmitted light. Alternative illumination schemes are possible (e.g. transillumination).

Spectroscope 12 has a dispersive element for separating the light into distinct wavelength signals in space and/or time, in one of the manners known in the art. The wavelength signals are of a predetermined bandwidth (determined by the limits of detection of the signals, a sampling interval, and properties of the dispersive element) Within the spectroscope 12, the wavelength signals are individually measured by one or more optical detectors using optical/electrical (O/E) signal conversion also known in the art.

The electrical signals corresponding to respective wavelength channels are then digitized, for example, using standard analog to digital (A/D) conversion. The A/D conversion determines the sample interval by effectively integrating or averaging over a duration of the respective wavelength channel in the electrical domain. The digitized channel signals may be processed in myriad of different ways, to reduce noise, correct for differences in efficiency of optical/electrical signal conversion of the different wavelengths, or remove other artifacts caused by the dispersive element, waveguide, and/or O/E conversion. The signal may further be corrected according to a receiver transformation function to correct for a difference between a standard spectral output of a known spectral trace, during a calibration process, all of which being conventional practice. Furthermore it is known to average over numerous samples of a same wavelength to provide a higher signal to noise ratio of the measurement.

While the invention may be practiced without A/D conversion, whereby the wavelength signals (either temporally multiplexed or as separate analog electrical signals) can be manipulated by analog circuitry, however a chief advantage of digitizing the wavelength signals is that digital spectral signals can be corrected and manipulated efficiently in conventional ways to provide a spectral trace, which can then be analyzed with analysis software using a spectral analyzer 14. The spectral analyzer 14 may be software resident on the computer for identifying center frequencies of peaks, computing areas under curves (AUCs), and moments about a given wavelength, and/or for decomposing spectral traces into components are well known in the art.

In accordance with the invention, the apparatus includes spectral analyzer 14 for analyzing a substantially whole curve measure of a bandshape attributed to a water band within periodontal tissue. The spectral analyzer 14 is a data processor executing program instructions for receiving a bandshape of a spectral component attributed to water identified from infrared absorption spectral data of a periodontal tissue, and deriving a substantially whole curve measure of the bandshape that varies with a state of the water molecules in the band, to provide an indicator of a condition of the tissue as healthy or subject to an inflammatory disease. For example the spectral analyzer 14 may compute a difference between a peak wavelength (point of maximum amplitude), mean, or other reference feature of the spectral trace and compare this with an expected value, or compare a weighted average, or a product or sum of the spectral trace with another function, to determine a difference, measure of fit, or ratio of the resulting product or value with an expected function or value.

The spectroscope 12 may be a spectrograph, in which case the spectral analyzer 14 and spectroscope 12 are integrated. Applicant notes that the spectral trace provided by typical spectrographs is continuous, in that successive pixels correspond to adjacent spectral bands, and this may be preferred so that the same apparatus can use spectral data outside of the water bands to identify other facets or manifestations of periodontitis or like inflammatory diseases (e.g. peri-implantitis and peri-implant mucositis), however, once a given set of spectral features are decided upon, the spectral regions required to identify these features may equally be obtained by less comprehensive spectral imaging.

By not capturing data at wavelengths that are not more relevant to the given spectral features than the wavelengths captured, the imaging and spectroscope's control architecture can be simplified, and/or operated to produce scans more quickly, or at a higher resolution, and a less expensive dispersive element may be used. The spectroscope 12 may, for example scan over smaller bandwidth ranges, and/or may identify fixed spectral peaks using filters.

It may further be possible to obtain bandwidths and center frequencies of spectral components using a plurality of filters in much the same way that multichromatic sensing permits color perception to eliminate wavelength scanning altogether. In principle, at least 2 wavelengths would be needed to provide reasonably high quality spectral data using filters, and precise knowledge of the passband of the optical filters would be required, although it would be normal to use a more points to provide higher accuracies, such as 4, 5, 6, 7, 8, 10, 12, 15, 20 or more. Naturally more than two wavelengths would be preferred to provide precise measures. If the variations of the bandshape have more than one degree of freedom, a corresponding number of additional wavelengths will be required to minimally determine the state of the molecules of the water band. Furthermore, by illumination of the site with only the frequencies desired, a number and quality of the filters may be reduced while providing equivalent signal information. Such a method involves determining absorption values of each of the at least two wavelengths and then fitting the absorption values to one of a plurality of known curves for the spectral components to extrapolate the bandshape of the water band from the absorption data. An indicator of the health/inflammatory diseased state of the site can then be derived according to a measure of fit of the absorption values to the known curves.

Spectral Features

While not wanting to be limited by the foregoing theory, to some extent it is known in the art that water absorption characteristics in the near infrared region (between 700-2500 nm) are sensitive to conditions of the water. The most prominent features of the water bands that vary with temperature are the bandwidths and peak center frequencies of the bands.

The principal spectral features of present interest are first and second OH stretching overtone/combination band centered around 1450 and 980 nm respectively, as well as the OH stretch-bend combination band, which occurs between 1800-2000 nm. While each of these three bands could be examined with different spectral regions, generally their strongest features (most immune to noise) are identifiable within the following spectral regions: 900-1100 nm, 1380-1560 nm, and 1800-2000 nm. Each of these bands are characterized by a shift in the band maximum to shorter wavelengths as the temperatures are increased and as the electrolyte concentration is varied.

Figure 2:
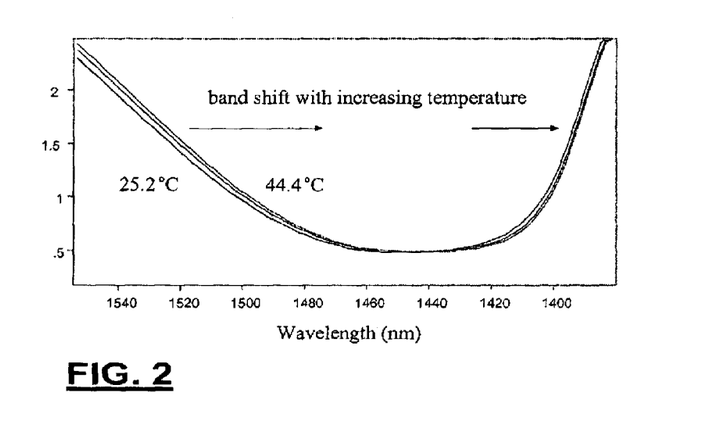
FIG. 2 is a schematic illustration of how a 1450 nm water band varies with temperature.

For example, FIG. 2 illustrates the impact of temperature change on the first OH stretching overtone/combination band (near 1450 nm). As the temperature of the water changes from 20 to 45° C., the first overtone/combination band maximum shifts from approximately 1451 nm to 1437 nm. Similar shifts are observed in the spectral band maxima of the near infrared vibrational transitions involving OH functional group.

These graphs were derived using methods and instrumentation as described in: M. G. Sowa, J. R. Payette and H. H. Mantsch, Near infrared spectroscopic assessment of tissue hydration following surgery. *J. Surgical Research* 86(1): 62-69, (1999). And in M Attas, M. D. Hewko, J. R. Payette, T. Posthumus, M. G. Sowa, and H. H. Mantsch, Visualization of cutaneous hemoglobin oxygenation and skin hydration using near infrared spectroscopic imaging. *Skin Res. Tech.* 7: 238-245, (2001). As well as E. M. Attas, M. G. Sowa, T. B. Posthumus, B. J. Schattka, H. H. Mantsch and S. L. Zhang, Near-IR spectroscopic imaging for skin hydration: the long and the short of it, *Biopolymers (Biospectroscopy,* 67: 96-106, (2002). These documents are incorporated herein by reference.

The OH stretching vibrational frequency and anharmonicity and thus the bandwidth of liquid phase OH stretching overtone/combination band and OH stretch-bend combination band are sensitive to the hydrogen bonding environment. In addition, the OH stretching bands have a complex rotational-vibrational structure leading to a complex associated temperature dependence in the overall bandshape. Furthermore, factors other than the temperature are known to influence the bandshape of water, such as electrolyte balance, which indicate that pH is also an important factor.

Inflammation is associated with a local elevation of tissue temperature which will impact the position and width of the water absorption bands while accumulation of water at the site of inflammation is expected to result in an increased intensity of the water bands. In the research results identified below, the intensity of the water bands (hydration index) was not found to correlate with the classification of sites as healthy, gingivitis or periodontitis, but there was a marked correlation between the width and center position of the water absorption bands as identified by moments of the water bands, especially the first moment. It is conjectured that increased temperature of the water at the site of inflammation is a principal causal factor for the noted correlation, although it may actually be a response to electrolyte or ionic bonding caused by dissolution of products of the infection or host response, for example.

Analysis Techniques

The preferred method for analysis involves decomposition of the spectral trace into components having known spectral contours, firstly to quantify the concentration of the respective components in the periodontal tissues, and secondly to isolate the characteristics such as bandshape and intensity of the individual absorption bands.

The changes in bandshape due to changes in tissue water temperature or hydrogen bonding environment can be summarized by calculating the underlying moments of the band. The $n^{th}$ order moments are computed using the following equation:

$$m_k(\lambda_0) = \int_{-\infty}^{\infty} (x - \lambda_0)^k f(x) dx \qquad \text{Eq. 1}$$

Where $\lambda_0$ is the wavelength about which the moment is taken. For present purposes, it may be taken to be a center wavelength of an expected peak of the specific band being investigated, or it may be a mean peak wavelength of the spectral component of tissue of a given condition, or a computed peak of the spectral trace.

The if k is null, the equation is that of the integral of the bandshape (a measure of hydration), and is not considered a moment herein.

The first moment is referred to herein as the centre of gravity of the band, and the second moment characterizes the width of the band. Higher order moments indicate the skewness of the band and determine the degree to which the band is pointy peaked or flat topped. It is noted that each moment is effectively the integral of the product of the spectral trace f(x) with a weighting function that is vanishingly small in the neighborhood of $\lambda_0$.

It will be appreciated by those of skill in the art that the moment can be taken to be about substantially any wavelength in theory, and that the value of $\lambda_0$ is effectively a marker with respect to which the measure of interest is taken, and the measure of interest is effectively a weighted average of the spectral trace.

These summary parameters of the absorption bands may be used as indices of hydration as well as indicators of the hydrogen bonding environment. These indices have been found to be sensitive to the underlying inflammation of the tissue and provide evidence for active periodontitis.

While the first moment was found useful for determining a distribution of the spectral trace, it is by no means the only manner of detecting the variation in NIR spectra as a function of condition of the water molecules in the tissue. Third and higher order odd moments are mathematically similar to the first order moment in that they all provide for vanishing values in the neighbourhood of $\lambda_0$, monotonically increasing weight for x as x increases above $\lambda_0$, and monotonically increasing negative weight for x as x decreases below $\lambda_0$. Even moments and comparisons of different moments can further be useful to identify certain features. In order to compute higher order moments smoothing of the bandshape or other noise cancellation is strongly advisable. Given the small dataset, and noise/uncertainty caused by smoothing functions, these have not been analyzed with the present dataset.

An alternative to using moment analysis about $\lambda_0$ is to compare the spectral trace with one of a plurality of curves, which may be determined experimentally or theoretically, such as a reference curve for the water band for water in a given condition. Furthermore a plurality of such reference curves may be provided, and a closest fit to these curves may provide an indicator of the disease state of the periodontal tissue at the site. For example, reference in-vitro measurements of a water containing tissue mimic could be acquired to comprise a set of reference curves that could be used to fit the resulting in-vivo tissue spectra. Several fitting strategies could be employed such as those taught in (Noninvasive Alcohol Testing Using Diffuse Reflectance Near-Infrared Spectroscopy, T. D. Ridder, S. P. Hendee, and C. D. Brown, Applied Spectroscopy, Vol. 59, Issue 2, pp. 181-189

What is notable about the spectral features of the water bands is that they are a subtle variation that affects the whole curve. The peak amplitude, or amplitude of the expected peak wavelength, and the integral of the spectral trace or bandshape, for example, which are the most frequently used features in spectroscopic analysis, are not useful differentiators. Accordingly, a whole curve measure, or substantially whole curve measure is most useful for measurement and identification of these changes. Examples of such whole curve measures include integrals of the spectral plots having different weighting functions, and regression analysis type measures of fit between the spectral plots and other curves. Selection of the weighting functions to emphasize the areas of the curve away from the peaks provides important information regarding these variations. The natural trade-off between increasing uncertainty of the measured spectra at lower amplitudes (nearer a noise floor) and the increasing divergence of the spectral curves in these areas (as shown in FIG. 2) cannot be solved, but can be statistically accounted for in numerous ways.

EXAMPLE

Thirty patients attending the Graduate Periodontics Clinics at the University of Manitoba, Canada participated in the study (17 males, 13 females, mean age 54.4 and SD 16.6). The research protocol was approved by each of the Research Ethics Boards of the University of Manitoba and the Institute for Biodiagnostics, NRC. Informed, written consent was obtained from each individual prior to collection of spectra.

Imaged sites were classified as being healthy, or having gingivitis, or periodontitis. Periodontitis sites were defined as those with periodontal probing depth=5 mm, clinical attachment loss=3 mm, and no bleeding on probing. Gingivitis sites were defined as those with periodontal probing depths<3 mm and bleeding on probing. Healthy sites were defined as those with periodontal probing depths<3 mm and no bleeding on probing. Any site that had an intermediate probing depth was excluded from the study. These clinical parameters were assessed by the same calibrated examiner (XMX).

Spectra were obtained from healthy sites contralateral to the diseased sites, or the nearest available site to the contralateral. All spectra were collected prior to clinical measurements from 26 periodontitis sites; 50 gingivitis sites; and 57 normal sites. All spectra used in the final data analyses were collected by the same operator (AM).

Acquisition of Optical Spectra

Figure 3:
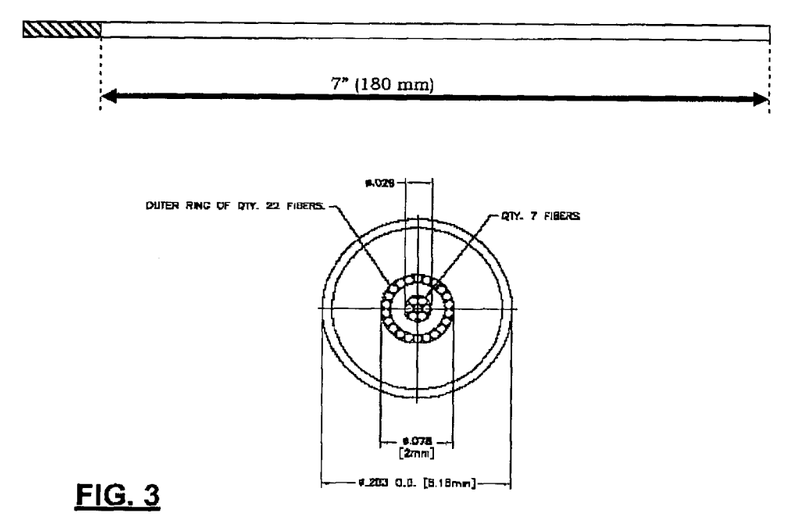
FIG. 3 is a schematic illustration of an intraoral probe used to obtain the results described in the experiment.

Spectra were collected using a portable PDA512-ISA spectrograph system (Control Development Inc., South Bend, Ind.) with a customized bifurcated fiber optic bundle, or "probe", designed for use in the oral cavity (Fiberguide Industries, Stirling, N.J.). The intraoral probe consisted of a 180 mm long stainless steel shaft, 5 mm in diameter, housing 29 fiber optic bundles, arranged as presented in FIG. 3. The sites were illuminated by a standard tungsten halogen light source which has broadband emission throughout the NIR spectrum.

Each reflectance spectrum analyzed consisted of 16 co-added scans, each scan being collected using a 0.03 s integration time (sampling interval). The spectral range between 500 and 1100 nm at 5 nm resolution was used. These specific parameters of spectral acquisition are not considered particularly efficacious for intraoral spectral imaging, and it is well known in the art that a shorter or longer integration time, different number of co-added scans, and different resolutions can all be varied considerably to achieve similar signal quality spectral images.

While the spectral range provided a single water band for analysis, it is known from FIG. 2 that the 1450 nm band and the OH stretch-bend combination band centered around 1950 (in the 1800-2000 nm region) also exhibits similar sensitivities to that of the 980 nm band, and is therefore considered equally applicable for this purpose. Each band is expected to undergo related subtle variations in response to changing temperature, pH etc., as they are, in part, artifacts of the same underlying stretching phenomenon of the OH functional group. Accordingly different spectral ranges are expected to be useful for identifying this aspect of periodontal diseases.

Preprocessing of the analyzed reflectance spectra involved calibrating the spectral acquisition equipment using a 99% Spectralon® reflectance standard (LabSphere, North Sutton, N.H.) to derive a correction for acquired reflectance spectra as is conventional practice.

During all NIR measurements, the subjects were comfortably seated and relaxed in a standardized semi-reclined position on a dental chair, in a quiet room with a constantly stable temperature.

Calculation of Inflammatory Indices from Optical—NIR Spectra

Figure 4:
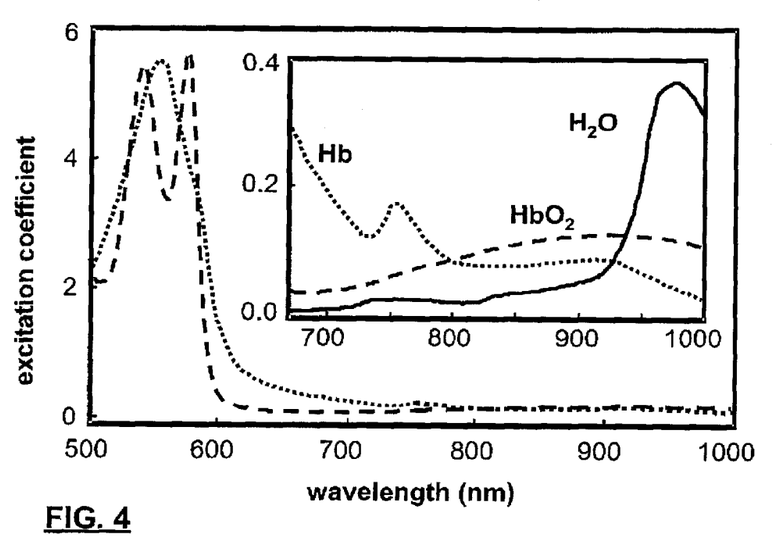
FIG. 4 is a plot of absorption as a function of wavelength for the three principal spectral components within a spectral range of the experiment.

A modified Beer-Lambert unmixing model that incorporates a nonparametric scattering loss function is used to determine the relative contribution of each component, Hb, $HbO_2$ and $H_2O$ to the spectral trace. FIG. 4 shows characteristic contours of these components in the spectral range of acquisition. Decomposition of the acquired spectra into these components is a standard way to quantify the components within the sample.

We have recently demonstrated that partial linear models show superior performance over parametric regression methods in the face of omitted variable bias or model mis-specification (M. G. Sowa, M. S. D. Smith, C. Kendall, E. R. Bock, A. C.-T. Ko, L-P. Choo-Smith and N. Stone, Semi-Parametric Estimation in the Compositional Modeling of Multicomponent Systems from Raman Spectroscopic Data, *Appl. Spectrosc* 60 (8), 877-883 (2006)). For the visible region between 510-620 nm where Hb and $HbO_2$ dominate the spectrum, the measured attenuation spectrum, $A_\lambda$, is modeled as a sum of 2 parametric terms, Hb and $HbO_2$, that contribute to the spectrum and a nonparametric term $m(\lambda)$ modeling a vector of covariates that have an unspecified functional form on the composite spectrum. It should be noted that $A_\lambda$ may be another name for $f(x)$ in Eq. 1, or $f(x)$ may be a residual of $A_\lambda$ with quantified amounts of other components (Hb, $HbO_2$) removed by decomposition. Within the IR segment of the imaging, the all three components are identifiable contributors.

$$A(\lambda) = \sum_{i=1}^{3} \xi_i(\lambda) c_i L + m(\lambda) + \text{error.} \quad \text{Eq. 2}$$

In the present model $m(\lambda)$ accounts for the Rayleigh and Mie scattering losses that contribute to the attenuation of measured light. Hb and $HbO_2$ concentrations per unit photon pathlength are recovered by using the noniterative method for estimation in partially linear models based on kernel smoothing first described by Speckman.[24] The combined spectral signatures of $HbO_2$ and Hb measures cutaneous blood volume total hemoglobin (tHb), an indicator of tissue perfusion, whereas the ratio of $HbO_2$ to tHb represents the oxygen saturation of the tissue ($S_tO_2$), as we have reported recently.[16,17,22,23] Therefore, $S_tO_2$ and tissue perfusion (tHb) are derived from the predicted Hb and $HbO_2$ concentrations, where: $[S_tO_2]=[HbO_2]/[tHb]$, and $[tHb]=[HbO_2]+[Hb]$.

The visible—short wavelength NIR spectrum of water in tissue is well-characterized[25] and dominates the near infrared region between 900-1050 nm. The moments are calculated for this strong absorption band of water centered at 980 nm. The integrated band intensity is water concentration-dependent[26] and is also computed and used as a tissue hydration index. The moments were calculated from the spectral traces directly without removing from the spectral traces, components of Hb and $HbO_2$. Other analyses have also been performed on residuals of the spectral traces with these components removed and similar results were obtained.

The first moment corresponds to the centre of gravity of the absorption band and has been shown to shift with tissue temperature and changes in electrolyte concentration and provides an index for the physical-chemical environment of the water in the tissue.

Figure 5:
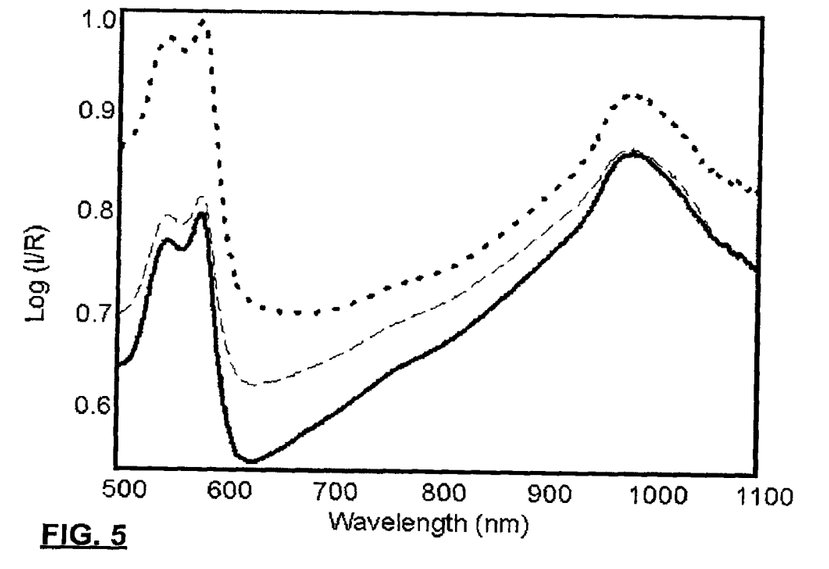
FIG. 5 is a plot of mean spectral traces of each of three groupings of sites: healthy, gingivitis and periodontitis.

FIG. 5 plots the average of the spectral traces of each of the three groups. It is noted that the periodontal sites are relatively well distinguished from the healthy (normal), and gingivitis sites.

Statistical Analysis

Inflammatory indices derived from optical spectral were analyzed separately using a one-way analysis of variance (ANOVA) to test the hypothesis that the indices from the three groups of sites: healthy, gingivitis and periodontitis, would differ significantly. Pairwise comparisons of mean differences between clinical groupings were made using separate pooled variance estimates for each pair of means with a Bonferroni adjustment for the total number of multiple comparisons. Statistical calculations were performed with Statistica 7.1 (Statsoft, Tulsa, Okla.).

Parametric receiver operating characteristic (ROC) curves were generated that plot the fraction of sites correctly predicted by each spectroscopy index to be a periodontitis site (sensitivity) versus the fraction of sites incorrectly predicted to be a periodontitis site (1-specificity) as the decision threshold for the index is varied between 0-∞. The ROC curve plots the trade-off in sensitivity and specificity of index as a function of decision threshold or cut-off value.[27] The area under the curve (AUC) is an indicator of the predictive power of the index for classifying periodontitis sites. An AUC=1 indicates a perfect classifier while an AUC=0.5 is expected for a random guess classifier. A binomial ROC model was used to generate the curves and determine the AUC of the curves. The binormal model assumes normally distributed test values for the periodontitis and the non-periodontitis groups of sites and uses the estimated population means and standard deviations from the two groups to generate the parametric ROC curve. The method by Hanley and McNeil[28] was used to compare AUC for ROC curves derived from the same cases. AUC between the ROC curves were considered significantly different if the 95% confidence intervals of the two AUCs did not overlap.

Results: Periodontal Inflammatory Indices Extrapolated from Spectra

Figure 6A:
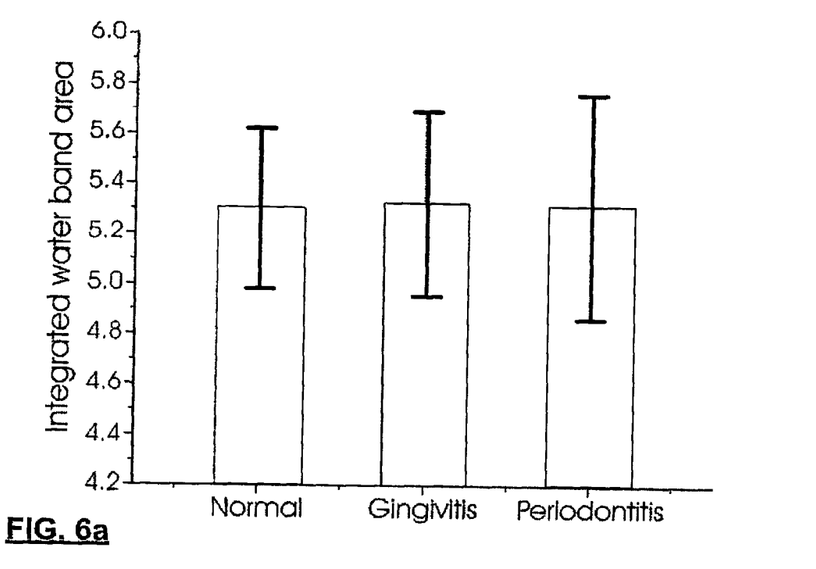
FIG. 6a,b,c are three bar graphs of computed means of three candidate indices for each of the three groupings of sites.
Figure 6B:
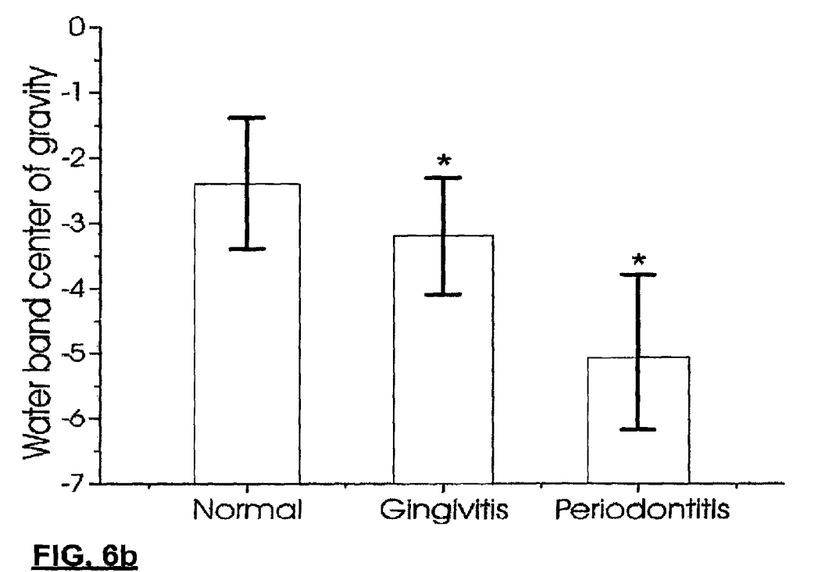
Figure 6C:
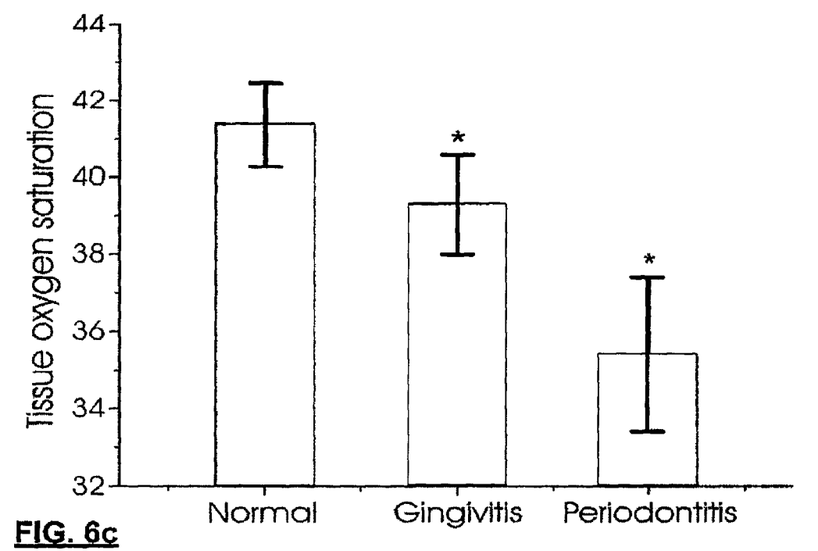

FIGS. 6a-c plot the mean and variance of respective proposed indices for each of the three groupings of sites extrapolated from the spectral traces. FIG. 6a plots the relative concentrations of the integrated water band area (hydration Index). It is surprising that the periodontal tissues do not show a higher degree of hydration, but will be evident by inspection, there is substantially no variation of this index between the groupings of sites.

FIG. 6b plots the COG index. There is a marked difference between periodontitis sites and normal sites given the uncertainties of the measures (p<0.03).

FIG. 6c plots $S_tO_2$, as computed from Hb and $HbO_2$ concentrations measured by the comparison of these curves. The tissue oxygenation in subjects with gingivitis and periodontitis are significantly decreased compared to controls (p<0.05). It will be noted that the $S_tO_2$ index is a better predictor of diseased state of the periodontal tissues than the center of gravity.

Accordingly the results show that detailed site-specific information on multiple aspects of periodontal inflammation can be extracted from NIR spectroscopic imaging and analysis. Similarly, we have found a statistically significant increase in Hb in the periodontitis sites compared to healthy (p<0.01) and gingivitis (p=0.05) sites. The tHb shows an increasing trend proceeding from healthy to gingivitis and periodontitis sites, but the trend is not statistically significant (p=0.07). The curves and the associate AUC are general indicators of the diagnostic utility of each index. The AUC for each index is reported in Table 1.

TABLE 1

| Index | AUC | SE | Lower 95% CI | Upper 95% CI |
|---|---|---|---|---|
| Hb | 0.6709 | 0.0039 | 0.6630 | 0.6788 |
| COG | 0.7225 | 0.0037 | 0.7151 | 0.7298 |
| $HbO_2$ | 0.5473 | 0.0041 | 0.5391 | 0.5556 |
| $S_tO_2$ | 0.8197 | 0.0028 | 0.8141 | 0.8253 |
| tHb | 0.5910 | 0.0041 | 0.5827 | 0.5993 |
| Hydration | 0.5050 | 0.0040 | 0.4969 | 0.5130 |

Figure 7:
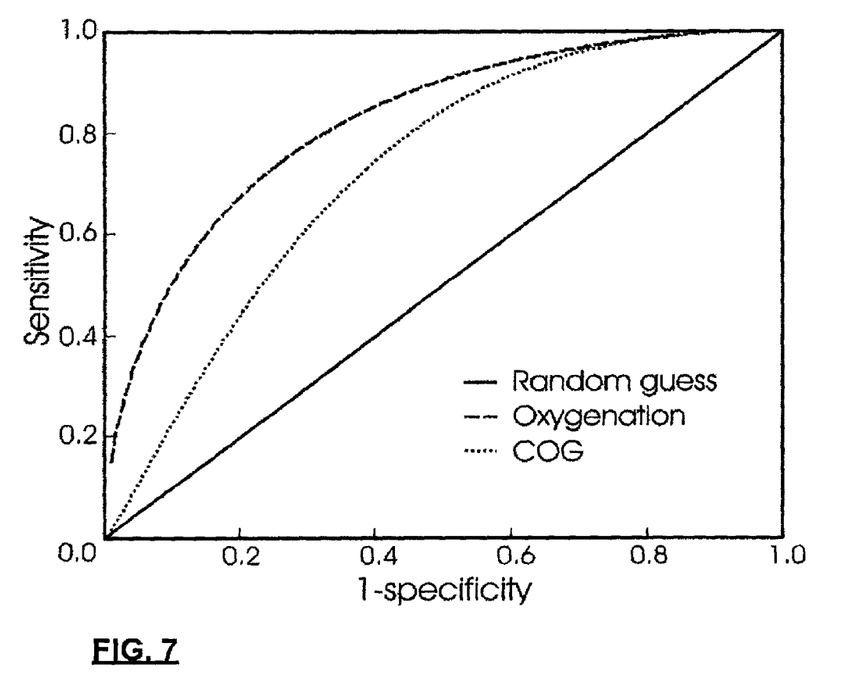
FIG. 7 is a graphical representation of sensitivity as a function of 1-specificity for two candidate indices: oxygen saturation and center of gravity of a 980 nm water band.

The AUC of an ROC curve is often used to indicate the general classification accuracy of a diagnostic test. In FIG. 7 the ROC curves show the general performance of two indices to distinguish periodontitis sites from non-periodontitis sites. Tests with AUCs in the range of 0.7 to 0.8 are generally considered fair. The AUC (0.72) of the index that measures the COG of the water absorption band (980 nm) falls into this category.

Diagnostic tests with AUCs between 0.8 to 0.9 are generally considered to be good tests. The tissue oxygenation shows a significantly greater AUC, 0.82, compared to the COG index and falls into this range. Examining the ROC curves, for a given specificity, the tissue oxygenation index consistently provides higher or equivalent sensitivity to the COG parameter for detecting periodontitis sites. If only a single index is used, tissue oxygenation provides the greatest discrimination between periodontitis and non-periodontitis sites. The optimal oxygen saturation threshold to use to detect periodontitis sites will depend on the desired trade-off in sensitivity versus specificity. If the false positive rate needs to be kept to a minimum, the optimal operating threshold will be toward the lower left of the ROC curve and the sensitivity of the index would be modest. However, if higher false positive rates are acceptable, the sensitivity improves dramatically.

For example in our study the sensitivity of the $S_tO_2$ index increases from approximately 65% to over 80% between false positive rates (1—specificity) of 20 to 40%.

Spectroscopy measures multiple indices simultaneously offering a potential increase in accuracy if multiple indices or features extracted from the spectra were used to establish diagnostic criteria. For example, the COG index alone shows modest diagnostic accuracy but is only weakly correlated with the $S_tO_2$ index (ρ=0.24) that shows good diagnostic accuracy. The weak correlation between tissue oxygenation and COG (given their different spectroscopic origins), suggest that these indices may probe different facets of the disease. One simple means of increasing the sensitivity would be to interpret these diagnostic tests in parallel by invoking an OR rule (diagnosis is positive if either $S_tO_2$ or COG is positive). The sensitivity of the combined result would be higher than either test individually but the specificity would be lower than that conveyed by either individual test. Combining the tests using the AND rule (diagnosis is negative is either $S_tO_2$ or COG is negative) enhances specificity relative to the individual tests at the expense of sensitivity.

Rather than analyzing these indices as univariate tests, a single test may be made explicitly combining the COG index with the oxygen saturation (or other indices) derived from the optical spectra to provide a multivariate classification model aimed to accurately diagnose diseased and healthy periodontal sites. However, the extension to multivariate classification requires a larger sample size than is currently available to us. These initial univariate analyses show that is likely that a multivariate classification model could be produced for NIR spectroscopic diagnostic of periodontal sites, and further show the unexpected value for COG parameters in such a model. Future studies with increased sample sizes may well develop diagnostic algorithms based on multiple indices and test their ability to separate the clinically-defined classes (i.e. healthy vs gingivitis vs periodontitis).

Our data clearly show that spectroscopy can monitor multiple inflammatory indices in periodontal tissues. However, in order to make it generally applicable, there are two immediate issues that require attention. The first is the issue of mucosal pigmentation. In highly pigmented skin the resolution of inflammatory indices by using spectroscopy is more complex because of the light absorption properties of melanin. This should not present a methodological barrier as inflammatory indices may still be readily measured in persons with heavy pigmentation, as we have recently addressed in skin.[23] However, further development is planned in order to address mucosal pigmentation by compensating for melanin in the intraoral environment. The second issue is that of tobacco smoking. Smoking is known to compromise overt inflammation in periodontal tissues,[19,29] and thus the confounding influence of tobacco smoke exposure on inflammation induced indices needs to be addressed. However, it should be noted that a further advantage of spectroscopy is that because carbon monoxygenated hemoglobin has a distinct visible spectrum,[30] the analysis of periodontal spectra may also be able to define the smoking status of individuals concurrently with diseases indices. Indeed, we have recently observed multiple alterations to the molecular and biochemical profile of serum from smokers and non-smokers.[31]

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

REFERENCES

1. Burt B. Position paper: epidemiology of periodontal diseases. *J Periodontol* 2005; 76:1406-1419.
2. Chun Y H, Chun K R, Olguin D, et al. Biological foundation for periodontitis as a potential risk factor for atherosclerosis. *J Periodontal Res* 2005; 40:87-95.
3. Tang Y T, Taylor G W, Scannapieco F, at al. Periodontal health and systemic disorders. *J Can Dent Assoc* 2002; 68:188-192.
4. Moutsopoulos N M, Madianos P N. Low-grade inflammation in chronic infectious diseases: paradigm of periodontal infections. *Ann N Y Acad Sci* 2006; 1088:251-264.
5. Armitage G C. Diagnosis of periodontal diseases. *J Periodontol* 2003; 74:1237-1247.
6. Socransky S S, Haffajee A D, Goodson J M, at al. New concepts of destructive periodontal disease. *J Clin Periodontol* 1984; 11:21-32.
7. Greenstein G. Commentary on periodontal diagnostic testing. *J Periodontol* 1995; 66:531-535.
8. Schacher B, Baron F, Rossberg M, et al. *Aggregatibacter actinomycetemcomitans* as indicator for aggressive periodontitis by two analysing strategies. *J Periodontol* 2007; 34:566-573.
9. Nozaki T, Kusumoto Y, Kitamura M, et al. A sensitive method for detecting *Porphyromonas gingivalis* by polymerase chain reaction and its possible clinical application. *J Periodontol* 2001; 72:1228-1235.
10. Pavolotskaya A, McCombs G, Darby M, at al. Sulcular sulfide monitoring: an indicator of early dental plaque-induced gingival disease. *J Dent Hyg* 2006; 80:11.
11. Takaishi Y, Morii H, Miki T. The benzoyl-DL arginine-naphthylamide (BANA) test and polymerase chain reaction measurement of pathogenic bacteria can assess the severity of periodontal disease. *Int J Tissue React* 2003; 25:19-24.
12. Prescher N, Maier K, Munjal S K, et al. Rapid quantitative chairside test for active MMP-8 in gingival crevicular fluid: first clinical data. *Ann N Y Acad Sci* 2007; 1098:493-495.
13. Lamster I B, Ahlo J K. Analysis of gingival crevicular fluid as applied to the diagnosis of oral and systemic diseases. *Ann N Y Acad Sci* 2007; 1098:216-229.
14. Taba M, Jr., Kinney J, Kim A S, et al. Diagnostic biomarkers for oral and periodontal diseases. *Dent Clin North Am* 2005; 49:551-571, vi.
15. Maiden M F, Tanner A C, Macuch P J, et al. Subgingival temperature and microbiota in initial periodontitis. *J Clin Periodontol* 1998; 25:786-793.
16. Sowa M G, Leonardi L, Payette J R, et al. Classification of burn injuries using near-infrared spectroscopy. *J Biomed Opt* 2006; 11:054002.
17. Sowa M G, Leonardi L, Payette J R, et al. Near infrared spectroscopic assessment of hemodynamic changes in the early post-burn period. *Burns* 2001; 27:241-249.
18. Loee H, Silness J. Periodontal Disease in Pregnancy. I. Prevalence and Severity. *Acta Odontol Scand* 1963; 21:533-551.
19. Scott D A, Singer D L. Suppression of overt gingival inflammation in tobacco smokers—clinical and mechanistic considerations. *Int J Dent Hyg* 2004; 2:104-110.
20. Otal E H, Iron F A, Andrade F J. Monitoring the temperature of dilute aqueous solutions using near-infrared water absorption. *Appl Spectrosc* 2003; 57:661-666.
21. Hanioka T, Shizukuishi S, Tsunemitsu A. Hemoglobin concentration and oxygen saturation of clinically healthy and inflamed gingiva in human subjects. *J Periodontal Res* 1990; 25:93-98.
22. Attas M, Hewko M, Payette J, et al. Visualization of cutaneous hemoglobin oxygenation and skin hydration using near-infrared spectroscopic imaging. *Skin Res Technol* 2001; 7:238-245.
23. Sowa M G, Matas A, Schattka B J, at al. Spectroscopic assessment of cutaneous hemodynamics in the presence of high epidermal melanin concentration. *Clin Chim Acta* 2002; 317:203-212.
24. Speckman P. Kernel smoothing in partial linear models. *J R Statist Soc B* 1988; 50 413-436.
25. Martin K. In vivo measurements of water in skin by near-infrared reflectance. *Applied Spectroscopy* 1998; 52:1001-1007.
26. Sowa M G, Payette J R, Mantsch H H. Near infrared spectroscopic assessment of tissue hydration following surgery. *J of Surg Res* 1999:86: 62-69.
27. Brown C D, Davis H T. Receiver operating characteristics curves and related decision measures. *Chemometrics Intellig Lab Systems* 2006; 80:24-38.
28. Hanley J A, McNeil B J. A method of comparing the areas under receiver operating characteristic curves derived from the same cases. *Radiology* 1983; 148:839-843.
29. Palmer R M, Wilson R F, Hasan A S, et al., Mechanisms of action of environmental factors—tobacco smoking. *J Clin Periodontol* 2005; 32 Suppl 6:180-195.
30. Araki R, Nashimoto I, Takano T. The effect of hyperbaric oxygen on cerebral hemoglobin oxygenation and dissociation rate of carboxyhemoglobin in anesthetized rats: spectroscopic approach. *Adv Exp Med Biol* 1988; 222:375-381.
31. Borden J T, Man A, Scott D A, et al. Tobacco-induced alterations to the Fourier-transform infrared spectrum of serum. *J Mol Med* 2003; 81:788-794.
32. Rosin M, Splieth C, Hessler M, at al. Quantification of gingival edema using a new 3-D laser scanning method. *J Clin Periodontal* 2002; 29:240-246.

The invention claimed is:

1. A method for obtaining data regarding a state of periodontal tissue, the method comprising:
    obtaining from the periodontal tissue, spectral absorption data of at least part of an infrared spectrum by illuminating the tissue with light of at least two wavelengths within a spectral range of a spectral component, and determining absorption values of each of the at least two wavelengths;
    identifying from the data a bandshape of the spectral component attributed to water; and
    deriving a substantially whole curve measure of the bandshape that varies with a state of the water molecules in the band other than a peak amplitude or integral of the bandshape, to provide an indicator of a disease state of the tissue other than a hydration index;
    wherein identifying the bandshape of the spectral component attributed to water further comprises fitting the absorption values to one of a plurality of known curves for the spectral components to extrapolate the bandshape from the absorption data; and
    wherein deriving the substantially whole curve measure comprises identifying the indicator of the condition of the tissue according to a measure of fit of the absorption values to the known curves.

2. The method of claim 1, wherein the spectral component is one of a OH stretching overtone and combination band, and a OH stretch-bend combination band, and the indicator is at least a contributory indicator of one of periodontitis, peri-implantitis and peri-implant mucositis.

3. The method of claim 2 wherein the contributory indicator is of periodontitis.

4. The method of claim 2 wherein the spectral component has a spectral range including at least a part of one or more of the following spectral ranges:

900-1100 nm, 1380-1560 nm, and 1800-2000 nm.

5. The method of claim 2 wherein the spectral component has a spectral range including at least a part of one or more of the following spectral ranges:

900-1100 nm, and 1380-1560 nm.

6. The method of claim 2 wherein the spectral component has a spectral range including at least a part of the 900-1100 nm spectral range.

7. The method of claim 2 wherein obtaining the spectral absorption data comprises illuminating the tissue with a broadband emitter that emits light within at least a part of a spectral range of the spectral component, and the absorption of the spectral component is sampled throughout the part of the spectral range to obtain a spectral trace.

8. The method of claim 2 wherein identifying the spectral component attributed to water further comprises decomposing the spectral trace to remove from the spectral trace contributions from respective other components known to absorb at wavelengths in the part of the spectral range to obtain the bandshape attributed to water.

9. The method of claim 2 wherein decomposing the spectral trace comprises applying a Beer-Lambert unmixing model, wherein quantified amounts of the other known constituents are removed from the signal.

10. The method of claim 2 wherein deriving the substantially whole curve measure of the bandshape comprises comparing the bandshape to at least one known curve for the spectral component, and identifying the indicator of the condition of the tissue according to a measure of similarity of the bandshape to the known curve.

11. The method of claim 2 wherein deriving the substantially whole curve measure of the bandshape comprises integrating the bandshape with a weighting function that weights wavelengths distant from a peak significantly differently than wavelengths near the peak.

12. The method of claim 11 wherein the integrating with a weighting function comprises computing a moment of the bandshape about a given wavelength.

13. The method of claim 12 wherein the given wavelength about which the moment is computed is one of an expected peak wavelength of the spectral component, a mean peak wavelength of the spectral component of tissue of a given condition, and a computed peak of the spectral trace.

14. The method of claim 11 wherein integrating the bandshape comprises computing a first moment of the spectral trace.

15. An article comprising a non-transitory computer readable memory and program instructions encoded on said memory for receiving a bandshape of a spectral component attributed to water identified from infrared absorption spectral data of a periodontal tissue, and deriving a substantially whole curve measure of the bandshape that varies with a state of the water molecules in the band, to provide an indicator of a condition of the tissue as healthy or subject to an inflammatory disease, where the indicator is not an index of hydration;

wherein identifying the bandshape of the spectral component attributed to water comprises fitting the absorption values to one of a plurality of known curves for the spectral components to extrapolate the bandshape from the absorption data; and wherein deriving the substantially whole curve measure comprises identifying the indicator of the condition of the tissue according to a measure of fit of the absorption values to the known curves.

16. The article of claim 15 wherein the program instructions derive the substantially whole curve measure by:

comparing the bandshape with at least one known curve for the spectral component, and identifying the indicator of the condition of the tissue according to a measure of similarity of the bandshape to the known curve; or integrating the bandshape with a weighting function that weights wavelengths distant from an expected peak differently than wavelengths near the expected peak to emphasize the areas of the curve away from the peaks.

17. The article of claim 15 wherein the program instructions are further adapted to:

preprocess spectral absorption data; or decompose a spectral trace to remove from the spectral trace contributions from respective other components known to absorb at wavelengths to obtain the bandshape attributed to water.

18. An apparatus for obtaining data regarding a state of periodontal tissue, the apparatus comprising a processor having program instructions for:

receiving spectral absorption data of at least part of an infrared spectrum from the periodontal tissue;

identifying from the data a bandshape of a spectral component attributed to water; and deriving a substantially whole curve measure of the bandshape that varies with a state of the water molecules in the band, to provide an indicator of a condition of the tissue as healthy or subject to an inflammatory disease other than a hydration index;

wherein identifying the bandshape of the spectral component attributed to water further comprises fitting the absorption values to one of a plurality of known curves for the spectral components to extrapolate the bandshape from the absorption data; and wherein deriving the substantially whole curve measure comprises identifying the indicator of the condition of the tissue according to a measure of fit of the absorption values to the known curves.

19. The apparatus of claim 18 wherein the spectral component is one of a OH stretching overtone and combination band, and a OH stretch-bend combination band.

20. The apparatus of claim 18 wherein the spectral component has a spectral range including at least a part of one or more of the following spectral ranges:

900-1100 nm, and 1380-1560 nm.

21. The apparatus of claim 18 wherein identifying the bandshape comprises decomposing a spectral trace of samples comprising the spectral component to remove from the spectral trace contributions from respective other components known to absorb at wavelengths in the part of the spectral range to obtain the bandshape attributed to water.

22. The apparatus of claim 18 wherein deriving the substantially whole curve measure of the bandshape comprises integrating the bandshape with a weighting function that weights wavelengths distant from an expected peak differently than wavelengths near the expected peak to emphasize the areas of the curve away from the peaks.

23. The apparatus of claim 20 wherein deriving the substantially whole curve measure of the bandshape comprises comparing the bandshape to at least one known curve for the spectral component, and identifying the indicator of the condition of the tissue according to a measure of similarity of the bandshape to the known curve.

\* \* \* \* \*